United States Patent [19]

Spohn et al.

[11] Patent Number: 5,003,088

[45] Date of Patent: Mar. 26, 1991

[54] METHOD FOR THE PREPARATION OF HALOPHTHALIC ANHYDRIDES

[75] Inventors: Ronald F. Spohn; Frank J. Sapienza, Jr., both of Getzville; Arthur H. Morth, Grand Island, all of N.Y.

[73] Assignee: Occidental Chemical Corporation, Niagara Falls, N.Y.

[21] Appl. No.: 393,449

[22] Filed: Aug. 14, 1989

Related U.S. Application Data

[63] Continuation-in-part of Ser. No. 160,033, Feb. 24, 1988, abandoned, and a continuation-in-part of Ser. No. 160,034, Feb. 24, 1988, abandoned.

[51] Int. Cl.$^5$ ............................................. C07D 307/89
[52] U.S. Cl. .................................. 549/246; 549/240; 549/247
[58] Field of Search ....................... 549/240, 246, 247

[56] References Cited

U.S. PATENT DOCUMENTS 4,559,405  12/1985  Telschow ............................ 549/240
4,560,773  12/1985  Telschow ............................ 549/240

OTHER PUBLICATIONS

Ohkrtsu et al, J. Japan Petrol. Inst., vol. 27 (1979) pp. 164–169.

Primary Examiner—Richard L. Raymond
Attorney, Agent, or Firm—James F. Tao; Arthur S. Cookfair

[57] ABSTRACT

Halophthalic anhydrides are prepared by reaction of chlorine with a saturated or partially saturated halophthalic anhydride at a temperature of 200° to 500° Celsius.

33 Claims, No Drawings

METHOD FOR THE PREPARATION OF HALOPHTHALIC ANHYDRIDES

BACKGROUND OF THE INVENTION

This application is a continuation-in-part application of copending applications Ser. No. 160,033 for "Improved Dehydrogenation Procedure"; and application Ser. No. 160,034 for "Selective Dehydrogenation with Chlorine," both now abandoned, both filed Feb. 24, 1988.

This invention relates to a process for the aromatization of a cyclic compound to form a fully aromatic ring structure. More particularly, it relates to a process for producing a halogen substituted phthalic anhydride from a halogen substituted saturated or partially saturated phthalic anhydride.

Substituted phthalic anhydrides are valuable raw materials for the synthesis of a variety of useful products. Halophthalic anhydrides are utilized as intermediates in the synthesis of organic polymers, dyes, plasticizers and in other uses.

The preparation of tetrahydrophthalic anhydrides and aromatization thereof by dehydrogenation under various conditions is known in the chemical literature. Skvarchenko et al., Obshchei Khimii, Vol. 30, No. 11. pp. 3535-3541 disclose the aromatization of chloro-substituted tetrahydrophthalic anhydride by heating with phosphorus pentoxide. In the aromatization process described, however, decarboxylation also occurs with the formation of the corresponding chloro-substituted benzene compound. The preparation of various other tetrahydrophthalic acids and anhydrides and various methods for dehydrogenation and aromatization thereof are reviewed by Skvarchenko in Russian Chemical Review. No. 1963, pp. 571-589.

U.S. Pat. No. 4,560,772 to Telschow discloses the reaction of 4-methyltetrahydrophthalic anhydride with excess sulfur and a catalytic amount of zinc oxide and 2-mercaptobenzothiazole to produce 4-methylphthalic anhydride and hydrogen sulfide.

U.S. Pat. No. 4,560,773 to Telschow discloses a similar reaction between the electron rich 4-methyltetrahydrophthalic anhydride and bromine in the presence of a catalytic amount of an acid acceptor such as dimethylformamide or pyridine in the liquid phase.

U.S. Pat. No. 4,517,372 to Tang, disclosed a process for the preparation of 4-fluorophthalic anhydride by dehydrogenation of gem-, difluoro- or gem-chlorofluoro- hexahydrophthalic anhydrides in the presence of a dehydrogenation catalyst such as palladium on carbon.

U.S. Pat. No. 4,709,056 to Cotter, Lin, and Pawlak discloses the preparation of 4,4-difluorohexahydrophthalic anhydride and 4-chloro-4-fluorohexahydrophthalic anhydrides by reaction of hydrogen fluorides with 4-chlorotetrahydrophthalic anhydride.

Ohkatou et al., *J. Japan Petrol. Inst.*. 22, 164–9 (1979) disclose the dehydrogenation of hydrocarbons using an activated carbon bed to produce the corresponding olefins. The mechanism of the reaction using cyclohexane and cyclohexene were studied using a pressure flow technique.

Bergmann *J. Amer. Chem. Soc.* 64, 176 (1942) discloses the aromatization of tetrahydrophthalic anhydride products of Diels-Alder reactions. The author discloses that dehydrogenation occurred when the tetrahydrophthalic anhydride product is boiled in nitrobenzene. However, it is further disclosed that dehydrogenation does not occur when p-bromonitrobenzene, p-chloronitrobenzene, or m-dinitrobenzene in xylene is employed. Moreover, it has been found that when the dihalohexahydrophthalic anhydrides of this publication are dehydrogenated in nitrobenzene, a portion of the nitrobenzene is reduced to aniline. The aniline reacts with the anhydride group of either the starting material or product to form imides and thus lower the yield of desired product.

SUMMARY OF THE INVENTION

In accordance with the present invention there is provided a process for the preparation of halogen substituted phthalic anhydrides of the formula

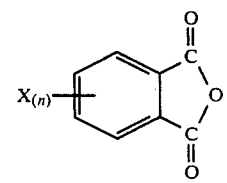

wherein each X is independently F—, Cl—, Br—, or I—, and n is 1 or 2, which comprises reacting chlorine with a halogen substituted hexa-, or tetra-hydrophthalic phthalic anhydride reactant of the formula

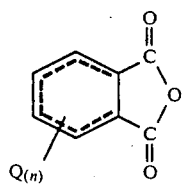

wherein Q is monohalo and is the same as X or is gem-dihalo, wherein at least one halogen is the same as X, and n is the same number as in formula I, with the proviso that each monohalo is directly attached to a double bond carbon and each gem-dihalo is directly attached to a non-double bond carbon, in liquid or vapor phase, at a temperature of 200°–500° C.

The structural formula

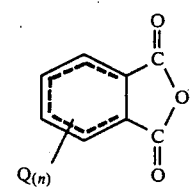

as employed herein represents saturated and partially saturated halo-phthalic anhydrides, including halotetrahydrophthalic anhydrides such as those of the formulae

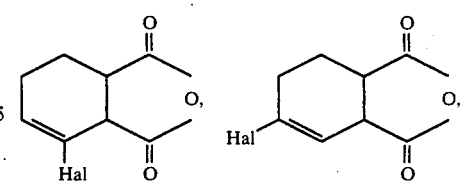

-continued

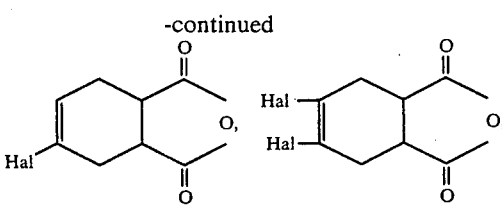

and the like, and gem-dihalohexahydrophthalic anhydrides such as those of the formulae

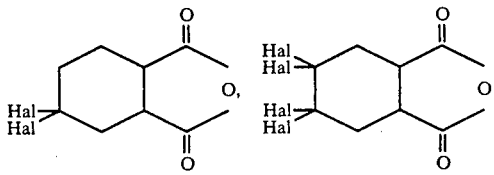

and the like, wherein Hal represents halogen.

In addition, it has further been found that unexpected improvements in yield may be achieved when the process of the invention is carried out either in the liquid or vapor phase, in the presence of an activated carbon catalyst.

The process of the invention may be exemplified by a preferred embodiment thereof, wherein 4-chlorophthalic anhydride is prepared by the vapor phase reaction of chlorine with 4-chlorotetrahydrophthalic anhydride in accordance with the following equation:

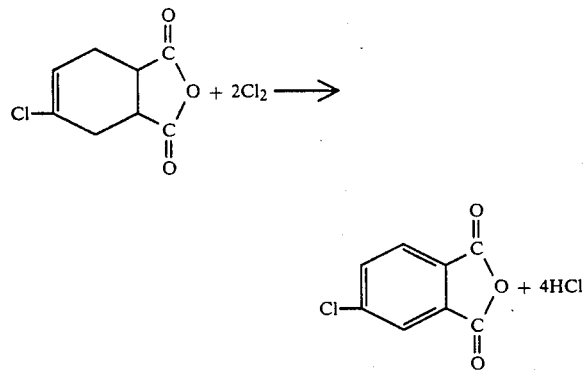

DETAILED DESCRIPTION OF THE INVENTION

The reactants employed in this invention can be prepared by various known methods. For example, the Diels-Alder addition reaction of a maleic anhydride with a conjugated diene produces an anhydride with a partially saturated six membered ring. Depending upon the desired product, the diene and/or the maleic anhydride may be selected which contain the appropriate halogen substituents. Various halogen substituted saturated or partially saturated phthalic anhydrides may be employed, as the anhydride reactant, including, for example:
4-chloro-1,2,3,6-tetrahydrophthalic anhydride;
4-fluoro-1,2,3,6-tetrahydrophthalic anhydride;
4-bromo-1,2,3,6-tetrahydrophthalic anhydride;
4-chloro-1,2,5,6-tetrahydrophthalic anhydride;
4-fluoro-1,2,5,6-tetrahydrophthalic anhydride;
-bromo-1,2,5,6-tetrahydrophthalic anhydride;
4,4-difluorohexahydrophthalic anhydride;
4,4-dichlorohexahydrophthalic anhydride;
4,4-dibromohexahydrophthalic anhydride;
3-chloro-1,2,5,6-tetrahydrophthalic anhydride;
3-fluoro-1,2,5,6-tetrahydrophthalic anhydride;
3-bromo-1,2,5,6-tetrahydrophthalic anhydride;
3,3-difluorohexahydrophthalic anhydride;
3,3-dichlorohexahydrophthalic anhydride;
3,3-dibromohexahydrophthalic anhydride;
4,5-dichloro-1,2,3,6-tetrahydrophthalic anhydride;
4,5-difluoro-1,2,3,6-tetrahydrophthalic anhydride;
4,5-dibromo-1,2,3,6-tetrahydrophthalic anhydride;
3,4-dichloro-1,2,5,6-tetrahydrophthalic anhydride;
3,4-difluoro-1,2,5,6-tetrahydrophthalic anhydride.

The corresponding iodo compounds may be employed, but are generally less stable and are not preferred.

The process may be carried out either in the vapor phase or the liquid phase. The vapor phase reaction is typically carried out in a tubular reactor, preferably of nickel, heated to a temperature sufficient to assist in the vaporization of the reactants and to maintain the vapor state. The halo-hydrophthalic anhydride reactant may be pumped into the tubular reactor as a liquid, vaporized in the reactor and passed through to the reaction zone simultaneously with chlorine gas to react and form the halophthalic anhydride product. Alternatively both reactants may be initially introduced into the reactor in the gaseous or vapor state. This may be accomplished, for example, by melting the organic reactant and sweeping the vapors into the reactor with a stream of nitrogen gas and mixing with chlorine therein. Alternatively, the chlorine gas may be used directly to sweep the organic vapors into the reactor. The two gases mix and react as they pass through the heated tube. The products are vented from the reaction tube and passed into a cool zone to allow the collection of the 4-chlorophthalic anhydride. The hydrochloric acid produced as a side product, may be trapped in an aqueous media. A more effective mixing of the gases may be achieved by causing the gases to pass through a porous, permeable medium, such as nickel mesh, placed n the reaction zone of the reaction tube to provide additional surface area.

If the process is carried out in the liquid or melt phase, the anhydride reactant may be maintained in the liquid state, with stirring, while chlorine gas is passed through, for example, by bubbling chlorine in below the surface of the liquid.

When the halo-hydrophthalic anhydride reactant is a chloro-substituted di- or tetra-hydrophthalic anhydride (or a gem-dichloro-hexahydrophthalic anhydride) the product will be a chloro-phthalic anhydride. When the halo-substituent of the anhydride reactant is other than chloro- the major product will be phthalic anhydride with the same halo-substituent as the starting reactant, however, minor amounts of chloro-substituted products may be formed. The amount of chlorine required will vary, depending on the starting material. If a halo-tetrahydrophthalic anhydride reactant is employed, two moles of chlorine will be required, while the use of a gem-dihalohexahydrophthalic anhydride will require three moles of chlorine per mole of anhydride reactant. However, it is preferred to employ a stoichiometric excess of chlorine.

The process is carried out at a temperature of 200° to 500° Celsius; preferred temperatures for the vapor phase reaction being in the range of 200° to 350° Celsius and for the liquid phase reaction, in the range of 200° to 250° Celsius. The process may be carried out at atmospheric, sub-atmospheric pressures. Super-atmospheric pressures may be employed, but are not generally preferred.

A solvent can be used in the reaction, but is generally not preferred. When a solvent is used, the anhydride reactant is dissolved in the solvent prior to introduction of the material to the reactor. In the vapor phase reaction, a lower boiling solvent is preferred, such as toluene or vinyl acetate. In the melt or liquid phase reaction, a higher boiling solvent such as 1,2,4-trichlorobenzene is preferred.

Advantageously, in a preferred embodiment, an activated carbon catalyst may be employed. A wide variety of activated carbon catalysts that may be employed in the present process are available commercially. Suitable catalysts include, for example, granular activated charcoals, such as those available from Calgon Corporation, Pittsburgh, Pa., designated Calgon F-300 (coal based); Calgon PCB (coconut-shell based); Calgon APC (coal bases); Norit MRX (peat based) and Norit KB activated carbon (peat based) available from American Norit Company, Jacksonville, Fla.; Carborundum GAC 40; Aldrich activated Carbon (Cat. No. 24,223-3) available from Aldrich Chemical Co., Milwaukee, Wis., or similar granular forms suitable for passing organic vapors through them. Alternatively, powdered forms of activated charcoal may be used. In a liquid phase process the activated carbon may be mixed with the liquid anhydride reactant. In the vapor phase process the mixture of gaseous and vapor reactants may be passed through a bed of the activated carbon particles.

The following specific examples are provided to further illustrate this invention and the manner in which it may be carried out. It will be understood, however, that the specific details given in the examples have been chosen for purposes of illustration and are not to be construed as a limitation on the invention. In the examples, unless otherwise indicated, all parts and percentages are by weight and all temperatures are in degrees Celsius.

EXAMPLE I

A U-shaped nickel reactor tube, ¾ inch inside diameter and 6 inches long on each side (an inlet side and an outlet side), was wrapped with heating tapes. A quantity of nickel mesh was placed within the outlet leg or side to increase the surface area and facilitate mixing of gaseous reactants. The inlet contained two openings; one for the chlorine feed and the second for the raw material feed. The outlet side of the reactor tube was connected to a series of receivers and traps to collect the product and entrap the acid side product. A quantity of 4-chlorotetrahydrophthalic anhydride was placed in a flask and heated, the melted material was transferred, in a steady flow by means of a pump, through heated lines to the inlet of the reactor tube. A flow of dry nitrogen was used to assist in the passage of materials through the reactor (20 ml/mm). The raw material was vaporized at 255° C. The reactor temperature was 240° to 300° C. Chlorine flow was 230 ml/min, and the organic flow was 0.15 grams/minute. The ratio of the flow of chlorine and the flow of organic were set at 2.5 moles of chlorine per mole of organic. The reaction was conducted under these temperatures and conditions and a product of 4-chlorophthalic anhydride was obtained at a 50% yield.

EXAMPLE II

To a three necked 50 ml round bottom flask, fitted with a stirrer, gas inlet tube and connected to a trap system, for recovery of products, was placed 20.38 g of 4-chloro-1,2,3,6-tetrahydrophthalic anhydride. The reactor was heated to 200° C. and illuminated with a 15 watt black, blue bulb (GE F15T8-BLB) with a transmission range of 300-400 nm and a maximum at 375 nm. An excess flow of chlorine was begun and the reaction continued for 8 hours. The reactor was purged with nitrogen and sampled. A 12% yield of 4-chlorophthalic anhydride was obtained.

EXAMPLE III

A U-shaped nickel reactor tube, 1 inch inside diameter and 30 inches long on each side, was wrapped with heating tapes. The input leg is used as the vaporizer; the outlet leg of the tube served as the reaction zone and was packed with 146 grams of activated carbon (Calgon F-300 manufactured by Calgon Corporation, Pittsburgh, Pa.). Reaction temperature was monitored by means of thermocouples and placed within the carbon bed. At the feed end of the U-shaped reaction tube were openings for the chlorine gas feed and for the anhydride reactant feed. The outlet of the reactor was connected to a series of receivers and traps to collect the product and entrap the anhydrous HCl produced. Liquid 4-chlorotetraphthalic anhydride was transferred, in a steady flow by means of a pump, through heated lines to the inlet of the reactor tube. Prior to starting, the pressure was reduced to 50 mm of Hg to lower the temperature of vaporization. The raw material was vaporized at 250° C. The reaction temperature was 240° to 250° C. Chlorine flow was 230 ml/min, and the organic flow was 0.67 grams/minute. The ratio of the flow of chlorine and the flow of organic was set at 2 moles of chlorine per mole of organic. The reaction was conducted under these temperatures and conditions and a product of 4-chlorophthalic anhydride was obtained at an 80% yield and 90% purity.

EXAMPLE IV

A mixture of 20 grams of 4-chlorotetrahydrophthalic anhydride and 5 grams of activated carbon, (NORIT KB) was placed in a reaction vessel containing a gas inlet tube, a stirrer and condenser and an outlet connected to a trap. The reactor was heated to 250° C. and a continuous flow of chlorine gas was passed through the liquid for 1.5 hours. Product began to collect in the trap, the temperature was reduced to 200° C., and stirring was continued for an additional hour. The yield of 4-chlorophthalic anhydride was 60% and analysis of the reaction mixture showed no starting material being present. The purity of the product was 60%.

EXAMPLE V

The procedure of Example III was repeated except that the feed was 4,4-difluorohexahydrophthalic anhydride, the vapor temperature was 240° C., reaction temperature was 255° C., the organic rate was 0.5 grams/minute, and the chlorine rate was 183 ml/min. The product, 4-fluorophthalic anhydride, was produced in 80% yield and 90% purity.

We claim:

1. A process for the preparation of halogen substituted phthalic anhydrides of the formula:

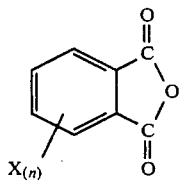

where each X is independently F—, Cl—, Br— or I—, and n is 1 or 2, which comprises reacting chlorine, in the absence of an acid acceptor, with a halogen substituted hexa- or tetra-hydrophthalic anhydride reactant of the formula:

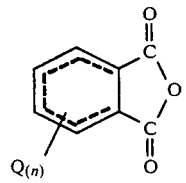

where Q is monohalo and is the same as X or is gem-dihalo, wherein at least one halogen is the same as X, and n is the same number as in formula I, with the proviso that each monohalo is directly attached to a double bond carbon and each gem-dihalo is directly attached to a non-double bond carbon, at a temperature of 200°-500° C.

2. A process according to claim 1 wherein X is F—, Cl—, or Br—.

3. A process according to claim 2, carried out in the vapor phase.

4. A process according to claim 2, carried out in the liquid phase at a temperature of about 200° to 300° Celsius.

5. A process according to claim 2 carried out in the presence of an activated carbon catalyst.

6. A process according to claim 5 carried out in the vapor phase.

7. A process according to claim 5 carried out in the liquid phase at a temperature of about 200° to 300° Celsius.

8. A process according to claim 7 wherein each Q is monohalo.

9. A process according to claim 2 wherein the reactant is 4-chlorotetrahydrophthalic anhydride.

10. A process according to claim 2 wherein the reactant is 3-chlorotetrahydrophthalic anhydride.

11. A process according to claim 2 wherein the reactant is 4-fluorotetrahydrophthalic phthalic anhydride.

12. A process according to claim 2 wherein the reactant is 4-bromotetrahydrophthalic anhydride.

13. A process according to claim 2 wherein the reactant is 4,5-dichlorotetrahydrophthalic anhydride.

14. A process according to claim 2 wherein the reactant is 4,5-difluorotetrahydrophthalic anhydride.

15. A process according to claim 2 wherein the reactant is 4-chloro-5-fluorotetrahydrophthalic anhydride.

16. A process according to claim 1, wherein at least one Q is gem-dihalo.

17. A process according to claim 16 wherein the reactant is 4,4-difluorohexahydrophthalic anhydride.

18. A process according to claim 16 carried out in the vapor phase.

19. A process according to claim 5 wherein each Q is monohalo.

20. A process according to claim 5 wherein at least one Q is gem-dihalo.

21. A process according to claim 19 carried out in the liquid phase.

22. A process according to claim 19 carried out in the vapor phase.

23. A process according to claim 22 wherein the reactant is 4-chlorotetrahydrophthalic anhydride.

24. A process according to claim 22 wherein the reactant is 3-chlorotetrahydrophthalic anhydride.

25. A process according to claim 22 wherein the reactant is 4-fluorotetrahydrophthalic anhydride.

26. A process according to claim 22 wherein the reactant is 4-bromotetrahydropthalic anhydride.

27. A process according to claim 22 wherein the reactant is 4,5-dichlorotetrahydrophthalic anhydride.

28. A process according to claim 22 wherein the reactant is 4,5-difluorotetrahydrophthalic anhydride.

29. A process according to claim 22 wherein the reactant is 4-chloro-5-fluorotetrahydrophthalic anhydride.

30. A process according to claim 20 wherein the reactant is 4,4-difluorohexahydrophthalic anhydride, and the process is carried out in the vapor phase.

31. A process for the preparation of 4-chlorophthalic anhydride which comprises mixing and reacting chlorine gas and 4-chloro-1,2,3,6-tetrahydrophthalic anhydride vapors, in the absence of an acid acceptor, at a temperature of about 240° to 300° Celsius.

32. A process according to claim 31 wherein a mixture of chlorine gas and 4-chloro-1,2,3,6-tetrahydrophthalic anhydride vapors are passed through a bed of activated carbon at a temperature of about 240° to 300° Celsius.

33. A process for the preparation of 4-fluorophthalic anhydride which comprises reacting a mixture of chlorine gas and 4,4-difluorohexahydrophthalic anhydride vapors at a temperature of about 240° to 300° Celsius, in the absence of an acid acceptor, in the presence of activated carbon.

* * * * *